United States Patent
Melamed et al.

(10) Patent No.: US 8,653,145 B2
(45) Date of Patent: Feb. 18, 2014

(54) METHOD FOR ALLEVIATING CLIMACTERIC SYMPTOMS

(75) Inventors: Hootan Melamed, Beverly Hills, CA (US); Edward Withrow, III, Santa Monica, CA (US); Jennifer Berman, Los Angeles, CA (US)

(73) Assignee: Eaton Scientific Systems, Ltd., Montecito, CA (US)

( * ) Notice: Subject to any disclaimer, the term of this patent is extended or adjusted under 35 U.S.C. 154(b) by 1165 days.

(21) Appl. No.: 11/523,975

(22) Filed: Sep. 19, 2006

(65) Prior Publication Data

US 2007/0066603 A1    Mar. 22, 2007

Related U.S. Application Data

(60) Provisional application No. 60/719,756, filed on Sep. 22, 2005.

(51) Int. Cl.
   *A61K 31/05* (2006.01)
   *C07D 451/00* (2006.01)

(52) U.S. Cl.
   USPC .................................. 514/734; 546/131

(58) Field of Classification Search
   USPC .................................................. 546/131
   See application file for complete search history.

(56) References Cited

U.S. PATENT DOCUMENTS

| | | | |
|---|---|---|---|
| 4,280,995 | A | 7/1981 | Loran |
| 4,680,172 | A | 7/1987 | Leeson |
| 5,112,604 | A | 5/1992 | Beaurline et al. |
| 5,599,557 | A | 2/1997 | Johnson et al. |
| 5,852,029 | A | 12/1998 | Fisher et al. |
| 6,156,771 | A | 12/2000 | Rubin et al. |
| 6,184,220 | B1 | 2/2001 | Turck et al. |
| 6,482,837 | B1 | 11/2002 | Wood |
| 6,682,747 | B1 | 1/2004 | Turck et al. |
| 6,747,043 | B2 | 6/2004 | Moran et al. |
| 6,919,092 | B2 | 7/2005 | Guittard et al. |
| 6,986,901 | B2 | 1/2006 | Meisel et al. |
| 2003/0108575 | A1 | 6/2003 | Lu |
| 2003/0187019 | A1 | 10/2003 | Ullah et al. |
| 2003/0191192 | A1 | 10/2003 | Venus et al. |
| 2003/0195179 | A1 | 10/2003 | Sawa |
| 2005/0009812 | A1 | 1/2005 | Seko et al. |
| 2005/0131079 | A1 | 6/2005 | Pujara |
| 2005/0136127 | A1 | 6/2005 | Meisel et al. |
| 2005/0272769 | A1 | 12/2005 | Linsell |
| 2006/0019991 | A1 | 1/2006 | McKinnell et al. |
| 2006/0270698 | A1* | 11/2006 | Furey et al. .................. 514/291 |
| 2007/0010550 | A1* | 1/2007 | McKenzie .................... 514/304 |

OTHER PUBLICATIONS

Goodman & Gilman's: The Pharmacological Basis of Therapeutics. 2001, pp. 450-451.*
Belchetz, P.E. (1994) Hormonal Treatment of Postmenopausal Women. N Engl J Med. 330 (15):1062-71.
Fitzpatrick, L.A. (2003) Alternatives to Estrogen Issue. Med. Clin. N. Am. 87(5):1091-1113.
(2004) Vasomotor Symptoms. Ob. Gyn. 104(Suppl. 4)106s-117s.
Greene, J.G. (1998) Constructing a Standard Climacteric Scale. Maturitas 29:25-31.
Hauser, G.A., Huber, I.C., Keller, P.J., Lauritzen, C., Schneider, H.P. (1994) Evaluation of Climacteric Symptoms (Menopause Rating Scale). Zentralbl. Gynakol. 116:16-23 [Article in German].
Krebs, E.E., Ensrud, K.E., Macdonald, R., Wilt, T.J., (2004) Phytoestrogens for Treatment of Menopausal Symptoms: A Systematic Review. Ob. Gyn. 104(4):824-836.
Potthoff, P., Heinemann, L.A., Schneider, H.P., Rosemeier, H.P., Hauser, G.A. (2000) The Menopause Rating Scale (MRS II): methodological standardization in the German population. Zentralbl. Gynakol. 122(5):280-286 [Article in German].
Remington: The Science and Practice of Pharmacy, Alfonso R. Gennaro, editor, 20th ed. Lippincott Williams & Wilkins: Philadelphia, PA, 2000.
Tice, J.A., Ettinger, B., Ensrud, K., Wallace, R., Blackwell, T., Cummings, S.R. (2003) Phytoestrogen Supplements for the Treatment of Hot Flashes: The Isoflavone Clover Extract (ICE) Study: A Randomized Controlled Trial. JAMA 290:207.
Uebelhack, R., Blohmer, J.-U., Graubaum, H.-J., Busch, R., Gruenwald, J., Wernecke, K.-D. (2006) Black Cohosh and St. John's Wort for Climacteric Complaints: A Randomized Trial. Ob. Gyn. 107(2): 247-55.
Rang, H. P. and Dale, M. M., Chrolinergic Transmission, Pharmacology, Second Volume, pp. 154-156, Churchill Livingstone, 1991, United States of America.

* cited by examiner

*Primary Examiner* — Renee Claytor
(74) *Attorney, Agent, or Firm* — Cislo & Thomas, LLP

(57) ABSTRACT

The present invention is a method for alleviating at least one climacteric symptom in a climacteric subject using an anticholinergic agent. To illustrate the instant invention, homatropine was shown to relieve hot flushes in peri-menopausal and post-menopausal women.

21 Claims, No Drawings

METHOD FOR ALLEVIATING CLIMACTERIC SYMPTOMS

This application claims the benefit of U.S. Provisional Patent Application Ser. No. 60/719,756, filed Sep. 22, 2005, the content of which is incorporated herein by reference in its entirety.

BACKGROUND OF THE INVENTION

Hot flushes, also known as hot flashes, and night sweats are common and salient symptoms experienced by menopausal woman that typically occur during the transition time from peri-menopause to menopause. They can continue to occur to up to 5 years post-menopause (75% of women experience hot flushes, and of those, 25% experience them for more than 5 years; Belchetz (1994) *New Engl. J. Med.* 330:1062-71). The "hot flush" is a result of sudden or acute drop in estrogen levels. This sudden drop can be due to natural events (menopause), or as a result of surgical (oophorectomy) or medical (hormone therapy, chemotherapy) removal of ovarian function. It is estimated that 80% of women undergoing natural or iatrogenic menopause experience hot flushes. Over time, the frequency and intensity of hot flushes do diminish, but they are still present in up to 50% of women for up to 5 years.

A hot flush is subjectively described as a sensation of intense warmth lasting as little as 30 seconds or as long as 5 minutes. It can be accompanied by tachycardia or palpitations, headache, faintness, or vertigo, and typically ends in profuse sweating and a cold sensation. At night, the frequency and severity of hot flushes increase, affecting a woman's sleep and ultimately her overall quality of life.

Estrogen therapy has been the mainstay of treatment for menopausal symptoms over the years, but concerns about the risks of hormone replacement therapy have made the search for alternative therapies critical for many women.

Mild symptoms may be improved by avoidance of triggering substances or situations. Caffeine, alcohol, spicy foods, and hot beverages may trigger hot flushes. Exercise, lowering stress levels, and smoking cessation are thought to help relieve the symptoms. Dressing in layers, wearing breathable clothing such as cotton and natural linen, and using fans, may also aid in comfort.

Studies investigating the benefits of dietary soy and vitamin E have mixed results as to the benefits on hot flashes (Krebs, et al. (2004) *Ob. Gyn.* 104:824-836). There is up to a 40% placebo effect in most studies on hot flashes, and randomized, blinded studies involving phytoestrogens derived from soy or red leaf clover do not show additional benefit (Fitzpatrick (2003) *Med. Clin. N. Am.* 87:1091-1113; Tice, et al. (2003) *JAMA* 290:207). There is a concern that phytoestrogens are not risk-free as they stimulate cellular activity in breast cysts and can contribute to postmenopausal bleeding.

Black cohash is an herbal supplement which has been shown to have benefit for hot flashes without altering FSH levels or endometrial thickness (Fitzpatrick (2003) supra; Tice, et al. (2003) supra). Side effects such as nausea, headaches, dizziness and liver toxicity have been reported (Fitzpatrick (2003) supra; Tice, et al. (2003) supra). A black cohash/St John's Wort combination has been shown to reduce the Menopause rating scale by 50% and the Hamilton Depression Scale by 41% (Uebelhack, et al. (2006) *Ob. Gyn.* 107:247-55).

There are no prescription medications that are as effective as estrogen for the treatment of hot flushes, but many have a positive impact in some women. Unfortunately, all have side effects that balance their clinical use. Venlafaxine, paroxetine, and fluoxetine have all shown an approximate 60% reduction in hot flushes but with side effects common to the SSRI's. Veralipride reduces hot flushes but caused weight gain and galactorrhea.

Clonidine has a 50% reduction in symptoms, but causes dry mouth, sedation and hypotension. Gabapentin has a 45% reduction in frequency, and 54% decrease in severity but can cause somnolence, fatigue, tremors, nausea, edema and ataxia. High dose progestins or megace may help, but can cause PMS symptoms, depression and fluid retention. Bellergal was used in the past, but has addictive potential (Fitzpatrick (2004) *Ob. Gyn.* 104:106s-117s).

The Women's Health Initiative (WHI) was the largest placebo controlled study of hormone replacement therapy to date, and showed an increase in thromboembolism, stroke, and breast cancer in the estrogen-progestin group, leaving many women with the uncomfortable feeling that they were compromising their long-term health by using hormone therapy.

In certain severe cases, medication is prescribed by a physician. Progestins such as megestrol acetate (Megace) have been prescribed. The hormone estrogen is the most effective treatment for hot flushes. It can help not only in this aspect, but also in lubricating the vagina and urinary tract, improving sexual function, and decreasing and preventing the incidence of urinary tract infections.

However, drawbacks of standard estrogen replacement therapy include the potential for increased risk of breast cancer, cardiovascular disease, general discomfort, and ineffectiveness. Recent studies have linked hormone replacement therapy to an increase risk of breast cancer. Furthermore, not all women can or want to take HRT, depending on their medical history and family history. Documenting the effectiveness of alternative treatments, and the development of new, non-hormonal treatments with low incidence of side effects and lower costs are desirable (Belchetz (1994) supra; Krebs, et al. (2004) supra; Fitzpatrick (2003) supra; Tice, et al. (2003) supra; Uebelhack, et al. (2006) supra; Fitzpatrick (2004) supra) At present, other than SSRI's which are marginally effective, there are no pharmaceutical or over the counter products that offer effective palliation of hot flushes.

U.S. Pat. Nos. 6,395,757 and 5,962,505 disclose the use of glycopyrrolate and glycopyrrolate analogs for alleviating menopausal hot flashes.

Accordingly, there is a need in the art for effective treatment regimes for relieving symptoms of the climacteric. The present invention meets this long-felt need.

SUMMARY OF THE INVENTION

The present invention is a method for alleviating at least one climacteric symptom in a climacteric subject. The method involves administering to a climacteric subject a therapeutically effective amount of an anticholinergic agent thereby alleviating at least one climacteric symptom in the subject. In some embodiments, the anticholinergic agent is homatropine, or a salt thereof.

DETAILED DESCRIPTION OF THE INVENTION

The climacteric is defined as the syndrome of endocrine, somatic and psychological changes occurring at the termination of the reproductive period in the female. According to the Greene Climacteric scale (Greene (1998) *Maturitas* 29:25-31), there are 21 common symptoms associated with a woman's climacteric stage, namely heart beating quickly or strongly, feeling tense or nervous, difficulty in sleeping, excitability, attacks of panic, difficulty in concentrating, feeling tired or lacking in energy, loss of interest in most things, feeling unhappy or depressed, crying spells, irritability, feeling dizzy or faint, pressure or tightness in head or body, parts of the body feel numb or tingling, headaches, muscle and joint pains, loss of feeling in hands and feet, breathing difficulties, hot flushes, sweating at night, and loss of interest in sex. Other symptoms commonly experienced in climacteric women include urinary frequency and urgency, palpitations, and anxiety.

It has now been found that anticholinergic agents, such as homatropine, alleviate hot flushes in peri-menopausal and post-menopausal women. In general, anticholinergic agents work by modulating the activity of muscarinic receptors which mediate a variety of cellular responses. For example, muscarinic receptors in smooth muscle regulate cardiac contractions, gut motility and bronchial constriction, whereas muscarinic receptors in exocrine glands stimulate gastric acid secretion, salivation and lacrimation. Muscarinic receptors also are found in the superior cervical ganglion, cerebral cortex, the striatum, the hippocampus, thalamus and brainstem.

Generally speaking, overstimulation of these receptors leads to diarrhea, frequent urination, miosis, bradycardia, bronchorrhea, emesis, lacrimation, and salivation. Other symptoms resulting from overstimulation of these receptors include nausea, vomiting, as well as eye pain, blurred or dim vision. Similarly, nicotinic stimulation causes muscle pain, tremors, weakness, hypertension, and fasciculations. Advantageously, anticholinergic agents result in antimuscarinic and antinicotinic actions. For example, anticholinergic agents are routinely given to people with urinary incontinence to prevent frequent urination (see, e.g., U.S. Pat. No. 6,919,092.

It is believed that anticholinergics act peripherally and not in the central nervous system, i.e., hypothalamus, to block the muscarinic receptors located on tissues which receive parasympathetic postganglionic nerves. One exception is the sweat glands; which receive sympathetic-cholinergic nerves. The hypothalamus is one of several brain areas that regulate the discharge rate of parasympathetic and sympathetic nerves by descending nerve fibers that synapse with either the parasympathetic preganglionic or sympathetic preganglionic nerves. It appears that the hypothalamus is the major brain area that regulates the discharge rate of the autonomic nerves (which may increase or decrease). The pathophysiology of how the decrease in estrogen affects the hypothalamic regulation of body temperature is largely unknown. However, not wishing to be bound by theory, it is believed that the anticholinergic agent disclosed herein modulates hypothalamic regulation of body temperature via muscarinic receptor activity thereby reducing climacteric symptoms such as hot flushes in climacteric subjects.

Accordingly, the present invention is a method for alleviating at least one climacteric symptom in a climacteric subject by administering to the climacteric subject a therapeutically effective amount of an anticholinergic agent, thereby alleviating at least one climacteric symptom in the climacteric subject. As used in the context of the present invention, "an anticholinergic agent" can be a compound that acts as an antagonist at the muscarinic receptor. In particular, the muscarinic receptor can be $M_1$ and/or $M_2$ muscarinic receptors. In particular embodiments, the anticholinergic agent can be a belladonna alkaloid including, but not limited to, atropine, scopolamine, methscopolamine, homatropine, hyoscyamine, wherein these compounds are normally administered as a salt, i.e., tertiary amines. For example, the atropine can be selected from a group consisting of atropine sulfate, atropine oxide, atropine-HCl salt, and methylatropine nitrate. The scopolamine can be selected from a group consisting of hydrobromide salt and methylbromide salt of scopolamine. The homatropine can be selected from a group consisting of hydrobromide salt and methylbromide salt of homatropine. The hyoscyamine can be selected from a group consisting of hydrobromide salt and sulfate salt of hyoscyamine. These agents, particularly the salt forms thereof, are readily available from a number of commercial sources or can be made or prepared according to standard methods well-known in the art. Salt forms of the identified anticholinergic agents are identified as follows:

Atropine, CAS-51-55-8 or CAS-51-48-1 (anhydrous form); atropine sulfate, CAS-5908-99-6; atropine oxide, CAS-4438-22-6 or its HCl salt, CAS-4574-60-1; and methylatropine nitrate, CAS-52-88-0.

Homatropine, CAS-87-00-3; hydrobromide salt, CAS-51-56-9; methylbromide salt, CAS-80-49-9.

Hyoscyamine (d, 1), CAS-101-31-5; hydrobromide salt, CAS-306-03-6; and sulfate salt, CAS-6835-16-1.

Scopolamine, CAS-51-34-3; hydrobromide salt, CAS-6533-68-2; methylbromide salt, CAS-155-41-9.

Other anticholinergic agents include ipratropium (e.g., as the bromide), sold under the name ATROVENT; oxitropium (e.g., as the bromide); and tiotropium (e.g., as the bromide) (CAS-139404-48-1). Also of interest are methantheline (CAS-53-46-3), propantheline bromide (CAS-50-34-9), anisotropine methyl bromide or Valpin 50 (CAS-80-50-2), clidinium bromide (QUARZAN, CAS-3485-62-9), isopropamide iodide (CAS-71-81-8), mepenzolate bromide (U.S. Pat. No. 2,918,408), tridihexethyl chloride (CAS-4310-35-4), and hexocyclium methylsulfate (CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO 01/04118 for other exemplary anticholinergic agents.

In particular embodiments, the anticholinergic agent is homatropine, or a salt thereof. While the hydrobromide salt of homatropine is well-known for use in ophthalmology as a cycloplegic and mydriatic and the 8-methyl derivative of homatropine hydrobromide is a well-known oral therapeutic for use as an antispasmodic and inhibitor of secretions, especially in gastrointestinal disorders, homatropine (including the hydrobromide and methylbromide salts) has not been described in the art for use in alleviating climacteric symptoms.

The amount of anticholinergic agent or salt thereof which is required to achieve a therapeutic effect will, of course, vary with the particular agent, the route of administration, the subject under treatment. The compounds of the invention can be administered in a dose ranging from 0.005 mg to 100 mg per day, or more suitably 0.05 mg to 50 mg per day, with the particular dose adjusted by a skilled clinician based on the severity of the symptoms and the subject being treated. Effectiveness of the dose employed can be ascertained by monitoring the subject based upon, e.g., the Menopause Rating Scale (MRS) and the Greene Climacteric Scale (GCS).

In accordance with the instant method, a therapeutically effective amount of an anticholinergic agent, such as a belladonna alkaloid, and in particular, homatropine, can be administered to a climacteric subject, which includes peri-menopausal and post-menopausal woman, wherein said effective amount alleviates, reduces, or ameliorates at least one climacteric symptom in the subject. Climacteric symptoms which can be alleviated by the anticholinergic agent include rapid heart beat, strong heart beat, feeling tense, feeling nervous, difficulty in sleeping, excitability, attacks of panic, difficulty in concentrating, feeling tired, lacking in energy, loss of interest in most things, feeling unhappy, feeling depressed, crying spells, irritability, feeling dizzy, feeling faint, pressure in head, pressure in body, tightness in head, tightness in body, numbness in a body part, tingling in a body part, headaches, muscle pains, joint pains, loss of feeling in hands, loss of feeling in feet, breathing difficulties, hot flushes, sweating at night, and loss of interest in sex. In some embodiments, the anticholinergic agent alleviates climacteric symptoms resulting from overstimulation of the muscarinic receptors. In particular embodiments, the muscarinic receptor is the $M_1$ or $M_2$ receptor. In other embodiments, the anticholinergic agent alleviates hot flushes. In a preferred embodiment, homatropine can be administered to alleviate hot flushes. In still other embodiments, the anticholinergic agent generally improves the quality of life (e.g., a decrease in night sweat episodes which affect a woman's sleep).

While it is possible for the anticholinergic agent or salt thereof to be administered alone, it is generally desirable to present it as a pharmaceutical formulation. Accordingly, the present invention further provides a method for alleviating at least one climacteric symptom, in particular, hot flushes, by administering to the climacteric subject a therapeutically effective amount of an anticholinergic agent, wherein the anticholinergic agent, such as belladonna alkaloid, in particular, homatropine, is administered in admixture with a pharmaceutically acceptable carrier, and optionally one or more other therapeutic ingredients. Another embodiment provides a method for alleviating at least one climacteric symptom, in particular, hot flushes, by administering to the climacteric subject a therapeutically effective amount of an anticholinergic agent, wherein the anticholinergic agent, such as belladonna alkaloid, in particular, homatropine, is administered in admixture with an excipient. Another embodiment provides for a method for alleviating at least on climacteric symptom, in particular, hot flushes, by administering to the climacteric subject a therapeutically effective amount of anticholinergic agent, such as belladonna alkaloid, in particular, homatropine, via oral, parenteral (including subcutaneous, intradermal, intramuscular, intravenous and intraarticular), intranasal, inhalation (including fine particle dusts or mists which may be generated by means of various types of metered dose pressurized aerosols, nebulisers or insufflators), rectal and topical (including dermal, buccal, sublingual and intraocular) administration although the most suitable route may depend upon for example the condition and symptom of the recipient subject. The formulations can conveniently be presented in unit dosage form and can be prepared by any of the methods well-known in the art of pharmacy. See, for example, Remington: The Science and Practice of Pharmacy, Alfonso R. Gennaro, editor, 20th ed. Lippincott Williams & Wilkins: Philadelphia, Pa., 2000. Accordingly, an embodiment of this invention is a method for alleviating at least one climacteric symptom in a climacteric subject by administering to the climacteric subject a therapeutically effective amount of an anticholinergic agent, thereby alleviating at least one climacteric symptom in the climacteric subject, wherein the anticholinergic agent, such as belladonna alkaloid, and in particular, homatropine, is administered via a mode selected from a group consisting of oral, parenteral, intranasal, inhalation, rectal and topical administration.

Suitable methods for preparing formulations include the step of bringing the active ingredient (i.e., the anticholinergic agent) into association with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

A tablet can be made by compression or molding, optionally with one or more accessory ingredients. Compressed tablets can be prepared by compressing in a suitable machine the active ingredient in a free-flowing form such as a powder or granules, optionally mixed with a binder, lubricant, inert diluent, lubricating, surface active or dispersing agent. Molded tablets can be made by molding in a suitable machine a mixture of the powdered compound moistened with an inert liquid diluent. The tablets can optionally be coated or scored and can be formulated so as to provide slow or controlled release of the active ingredient therein.

Formulations for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents. The formulations can be presented in unit-dose or multi-dose containers, for example sealed ampoules and vials, and can be stored in a freeze-dried (lyophilized) condition requiring only the addition of the sterile liquid carrier, for example saline or water-for-injection, immediately prior to use. Extemporaneous injection solutions and suspensions can be prepared from sterile powders, granules and tablets of the kind previously described.

Dry powder compositions for topical delivery to the lung by inhalation can, for example, be presented in capsules and cartridges of for example gelatin, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge can contain the active ingredient in combination with another therapeutically active ingredient. Alternatively, the compound of the invention can be presented without excipients. Packaging of the formulation can be suitable for unit dose or multi-dose delivery. In the case of multi-dose delivery, the formulation can be pre-metered (e.g., as in DISKUS, see GB 2242134 or DISKHALER, see GB 2178965, GB 2129691 and GB 2169265) or metered in use (e.g., as in TURBUHALER, see EP 69715). An example of a unit-dose device is ROTAHALER (see GB 2064336). The DISKUS inhalation device comprises an elongate strip formed from a base sheet having a plurality of recesses spaced along its length and a lid sheet hermetically but peelably sealed thereto to define a plurality of containers, each container having therein an inhalable formulation containing an anticholinergic agent of the invention preferably combined with lactose. Desirably, the strip is sufficiently flexible to be wound into a roll. The lid sheet and base sheet will preferably have leading end portions which are not sealed to one another and at least one of the said leading end portions is constructed to be attached to a winding means. Also, the hermetic seal between the base and lid sheets extends over their whole width. The lid sheet can desirably be peeled from the base sheet in a longitudinal direction from a first end of the said base sheet.

Spray compositions for topical delivery to the lung by inhalation can, for example, be formulated as aqueous solutions or suspensions or as aerosols delivered from pressurized packs, such as a metered dose inhaler, with the use of a suitable liquefied propellant. Aerosol compositions suitable for inhalation can be either a suspension or a solution and generally contain the anticholinergic agent optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas can also be used as propellant. The aerosol composition can be excipient free or can optionally contain additional formulation excipients well-known in the art such as surfactants, e.g., oleic acid or lecithin and cosolvents, e.g., ethanol. Pressurized formulations will generally be retained in a canister (e.g., an aluminium canister) closed with a valve (e.g., a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced can be size reduced by conventional means e.g., by micronisation. The desired fraction can be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Solutions for inhalation by nebulation can be formulated with an aqueous vehicle with the addition of agents such as acid or alkali, buffer salts, isotonicity adjusting agents or antimicrobials. They can be sterilized by filtration or heating in an autoclave, or presented as a non-sterile product.

Formulations for rectal administration can be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

The invention is described in greater detail by the following non-limiting examples.

Example 1

Identification of Homatropine for Alleviating Hot Flashes

Eight peri-menopausal and post-menopausal women receiving the anti-tussive HYCODAN (one teaspoon every four to six hours as needed), reported relief of hot flushes while taking this medication. HYCODAN is composed of hydrocodone bitartrate (5 mg) and homatropine methylbromide (1.5 mg) in each tablet or 5 cc of suspension. The active ingredient responsible for the relief of hot flash symptoms was subsequently isolated by a pharmacist and found to be homatropine methylbromide.

Example 2

Efficacy of Anticholinergic Agent for Alleviating Climacteric Symptoms

Study Objective. A single-center, prospective, randomized, double-blind, dose escalation, placebo-controlled, parallel-group-design clinical trial of homatropine versus placebo is carried out in subjects who are experiencing hot flushes and night sweats. Subjects are recruited from the general population based upon inclusion and exclusion criteria.

Inclusion Criteria.

i. The subject is aged 45-65.

ii. The subject has given written informed consent to participate in the study.

iii. The subject is menopausal or post-menopausal. (Defined as FSH greater than 40, and absence of menses for at least:

The prior 2 months before screening, and 6 of 12 months before screening.

iv. The subject reports episodes of hot flushes and/or night sweats affecting their quality of life, as determined by items 1 and 3 of the Menopause Rating Scale (Hauser, et al. (1994) *Zentralbl. Gynakol.* 116:16-23; Potthoff, et al. (2000) *Zentralbl. Gynakol.* 122:280-286).

v. The subject is willing to report the number of episodes of hot flushes and/or night sweats on a daily bases.

vi. The subject must be able to successfully complete all study-related instruments, including all questionnaires.

vii. The subject, as agreed by the primary medical investigator, meets all specific inclusion and exclusion study criteria.

viii. The subject has a personal history of breast or uterine cancer, or any medical condition which precludes hormone replacement therapy as a treatment option for climacteric symptoms.

ix. The subject is willing and able to provide documentation of a normal pelvic exam and Pap smear within the past 12 months.

x. The subject has not been receiving any over the counter or prescription for the past 3 months that may influence hot flashes.

xi. Not receiving hormone replacement therapy (HRT) for the past 3 months.

xii. Not receiving any medication to treat hot flushes for the past 3 months.

No herbal treatments or remedies

SSRI therapy for more than 3 months due to anxiety or depression is allowed

No other anticholinergic medications

Other medications are acceptable for inclusion, with approval.

xiii. Self-reported frequency of hot flushes of at least 35 per week.

Exclusion Criteria.

i. Unwillingness or inability to comply with any aspect of the clinical trial protocol.

ii. The subject is allergic to, or expresses problems with, ingredients in homatropine methylbromide or placebo.

iii. Primary glaucoma (or any family history of glaucoma), or subjects with narrow angle or close angle glaucoma.

iv. Hypersensitivity to belladonna alkaloids.

v. Abnormal muscle weakness or myasthenia gravis.

vi. Subjects who have experienced or have thyrotoxicosis.

vii. Cardiovascular disease defined as:

history of myocardial infarction, stroke, transient ischemic attack (TIA), carotid or other peripheral vascular disease, uncontrolled hypertension, a strong family history of heart attack before age 55, or instance of life-threatening arrhythmia within the past six months.

viii. Insulin-dependent diabetes.

ix. Clinically significant hematological, renal or hepatic abnormalities.

x. Active cancer, other than breast or endometrial.

xi. Pulmonary disease of any type.

xii. Self-reported history of alcohol or controlled substance abuse within the past year.

xiii. Current use of methadone, anti-coagulants, or other similar medications.

xiv. Currently taking or using psychotropic drugs or trazodone.

xv. Subjects on SSRI's are allowed into the study as long as their dosage has been stable for at least three consecutive months prior to study entry.

xvi. Abnormal pap smear within the past 12 months.

xvii. Severe vaginal or pelvic symptomatology.

xviii. Any clinically significant abnormality from the screening physical examination or safety laboratory test results.

xix. Any medical condition, psychological condition, or social circumstance that would impair her ability to participate in the study, or who may increase the risk to herself or others by participating.

xx. Psychological or psychiatric therapy of depressive symptoms during the study (except for pre-existing SSRI therapy as noted).

xxi. Use of any experimental (i.e., non-approved) drug within the past three months.

xxii. The subject has a disease or condition that compromises the integrity of the clinical trial or the safety of the subject.

Study Design.

After screening, a 2-week placebo run-in is carried out and eligible subjects are randomized at baseline and receive either homatropine or a placebo for a 12-week period. The homatropine group receives an oral suspension composed of 1.5 mg/5 cc homatropine, syrup (water and sugar) and pineapple and tropical punch artificial flavoring. Randomization is at an equal ratio of 1:1. As the study is a dose escalating study, the percentages and the concentration of homatropine remains the same, while the amount taken changes. Subjects are asked to take the oral suspension at 3 to 4 times per day (i.e., a total of 4.5 to 6 mg homatropine per day). Subjects are asked to maintain their normal diet and exercise regimen during the 12-week study period. Subjects follow a protocol dose escalation schedule without the opportunity to increase the dose during the study based on symptoms/efficacy. Blood samples are obtained during the screening visit (and again at the last visit) for CBC, Lipid panel, hepatic profile, and serum hormone levels including FSH, Estradiol, Total and Free testosterone.

Evaluation of Symptoms.

Subjects undergo a focused physical examination (vital signs and review of systems). Blood tests for hormone levels, CBC, lipid panel, and hepatic profile are conducted at the first visit (baseline), and at the end of the study. Subjects are asked to complete self-reporting questionnaires (MRS, GCS, and AUASS) at baseline, 6 weeks, and 12 weeks. Subjects are asked to undergo a Beck Depression Index assessment and complete a Quality of Life Assessment (SF-36) at baseline and at the end of the study. Subjects are asked to log the number of episodes of hot flushes and/or night sweats and other subjective symptoms on a daily basis.

Menopause Rating Scale (MRS) is a validated questionnaire listing symptoms associated with menopause. Subjects report on number, frequency and intensity of symptoms on this validated questionnaire.

Greene Climacteric Scale (GCS) is a validated questionnaire that looks at the total score and subscores of the psychological, physical, and vasomotor symptoms during menopause.

Urinary AUA-SYMPTOM SCORE (AUASS) is a validated questionnaire administered at all clinical visits from to help the patient determine how bothersome their urinary symptoms are and to check the effectiveness of treatment.

Beck Depression Index is a validated assessment administered at baseline and at the end of the study to assess the degree of signs and symptoms associated with clinical depression.

SF-36 is a validated questionnaire administered at baseline and at the end of the study to assess subjective general quality of life indicators.

Study Results.

The primary safety variables are adverse events encountered by the study-population. However, because widespread usage of homatropine is already present with no notable adverse effects noted, efficacy of homatropine is of primary relevance.

The assessments of adverse events and research staff measurements are compared within subjects from reports and measurements at baseline, 4 weeks, 8 weeks, and 12 weeks. A comparison between the homatropine group and placebo group is made for the assessable subject population. Additional analyses are conducted on the intent-to-treat population to compare the mean change from baseline in the two groups. The overall incidence rates are compared between treatments using Pearson's chi-square tests or Fisher's-Exact tests.

The efficacy and safety variables assessing the homatropine versus placebo are the difference-of-means defined as the change from baseline as collected subsequent visits. Categorical variables are analyzed by the Mantel-Haenszel chi-square test except for small cell sizes where Fisher's exact two-tail chi-square test is used. Continuous variables are analyzed by the two-sample t-test. Examples of categorical variables include diabetes, hypertension, and income. Examples of continuous variables include age, weight, and average co-morbid risk.

Continuous data is analyzed both as continuous and as categorical data. For example, energy can be assessed as the difference-of-means between an active product versus placebo group, but can also be classified as those subjects with energy of less than 2 (0 to 9 scale), a categorization of subjects considered in low energy. Assessments of a given variable both for means and for categories can be useful, since the means can hide important differences between groups by disguising the tails of distribution.

The results of this analysis demonstrate efficacy of using homatropine to decrease hot flushes and increase quality of life.

What is claimed is:

1. A method for treating at least one climacteric symptom in a climacteric subject in need thereof, comprising the step of:
administering to the climacteric subject a therapeutically effective amount of homatropine at a dose of approximately 0.05 mg/day to approximately 100 mg/day, thereby alleviating at least one climacteric symptom in the climacteric subject.

2. The method of claim 1, wherein the homatropine is a methylbromide salt of homatropine.

3. The method of claim 1, wherein the climacteric symptom is selected from the group consisting of rapid heart beat, strong heart beat, feeling tense, feeling nervous, difficulty in sleeping, excitability, difficulty in concentrating, feeling tired, lacking in energy, loss of interest in most things, feeling unhappy, crying spells, irritability, feeling dizzy, feeling faint, pressure in head, pressure in body, tightness in head, tightness in body, numbness in a body part, tingling in a body part, headaches, muscle pains, joint pains, loss of feeling in hands, loss of feeling in feet, breathing difficulties, hot flushes, sweating at night, and loss of interest in sex.

4. The method of claim 1, wherein the climacteric symptom is hot flushes.

5. The method of claim 1, wherein the homatropine is administered in admixture with a pharmaceutically acceptable carrier.

6. The method of claim 1, wherein the homatropine is administered in admixture with an excipient.

7. The method of claim 1, wherein the homatropine is administered via a mode selected from a group consisting of oral, parenteral, intranasal, inhalation, rectal and topical administration.

8. The method of claim 2, wherein the therapeutically effective amount of homatropine methylbromide is up to approximately 5 mg/day.

9. The method of claim 2, wherein the climacteric symptom is selected from the group consisting of rapid heart beat, strong heart beat, feeling tense, feeling nervous, difficulty in sleeping, excitability, difficulty in concentrating, feeling tired, lacking in energy, loss of interest in most things, feeling unhappy, crying spells, irritability, feeling dizzy, feeling faint, pressure in head, pressure in body, tightness in head, tightness in body, numbness in a body part, tingling in a body part, headaches, muscle pains, joint pains, loss of feeling in hands, loss of feeling in feet, breathing difficulties, hot flushes, sweating at night, and loss of interest in sex.

10. The method of claim 2, wherein the climacteric symptom is hot flushes.

11. The method of claim 2, wherein the homatropine methylbromide is administered in admixture with a pharmaceutically acceptable carrier.

12. The method of claim 2, wherein the homatropine methylbromide is administered in admixture with an excipient.

13. The method of claim 2, wherein the homatropine methylbromide is administered via a mode selected from a group consisting of oral, parenteral, intranasal, inhalation, rectal, and topical administration.

14. The method of claim 4, wherein the therapeutically effective amount of homatropine is up to approximately 50 mg/day.

15. The method of claim 4, wherein the homatropine is selected from a group consisting of a hydrobromide salt and a methylbromide salt of homatropine.

16. The method of claim 4, wherein the homatropine is administered in admixture with a pharmaceutically acceptable carrier.

17. The method claim 4, wherein the homatropine is administered in admixture with an excipient.

18. The method of claim 4, wherein the homatropine is administered via a mode selected from a group consisting of oral, parenteral, intranasal, inhalation, rectal and topical administration.

19. The method of claim 1, wherein the climacteric symptom arises from a drop in estrogen levels in the climacteric subject.

20. The method of claim 2, wherein the climacteric symptom arises from a drop in estrogen levels in the climacteric subject.

21. The method of claim 15, wherein the climacteric symptom arises from a drop in estrogen levels in the climacteric subject.

* * * * *